(12) United States Patent
Bastia

(10) Patent No.: US 8,308,742 B2
(45) Date of Patent: *Nov. 13, 2012

(54) DEVICE FOR ELASTIC LIGATURE OF TISSUES

(75) Inventor: Filippo Bastia, Carpi (IT)

(73) Assignee: THD S.p.A., Correggio (IT)

( * ) Notice: Subject to any disclaimer, the term of this patent is extended or adjusted under 35 U.S.C. 154(b) by 236 days.

This patent is subject to a terminal disclaimer.

(21) Appl. No.: 12/716,320

(22) Filed: Mar. 3, 2010

(65) Prior Publication Data

US 2010/0234949 A1    Sep. 16, 2010

(30) Foreign Application Priority Data

Mar. 12, 2009  (IT) ............................... RE2009A0021

(51) Int. Cl.
*A61B 17/10* (2006.01)
(52) U.S. Cl. ...................................................... 606/140
(58) Field of Classification Search .......... 606/139–141, 606/151, 157; 128/830, 842
See application file for complete search history.

(56) References Cited

U.S. PATENT DOCUMENTS

| 3,382,873 | A | 5/1968 | Banich et al. |
| 7,722,627 | B2* | 5/2010 | Andreen ........................ 606/140 |

FOREIGN PATENT DOCUMENTS

| DE | 19834263 A1 | 2/2000 |
| EP | 0181976 A | 5/1986 |
| EP | 1155660 A | 11/2001 |

* cited by examiner

*Primary Examiner* — Melanie Tyson
(74) *Attorney, Agent, or Firm* — Pearne & Gordon LLP

(57) ABSTRACT

A device for elastic ligature of tissues has a first and a second element, one of which exhibits a support portion for at least a rubber ring. The elements are slidably coupled to one another such that a reciprocal sliding between the elements determines a release of a rubber ring from the support portion. A trigger is manually maneuverable by an operator and acts on the second element for realising a reciprocal sliding between the elements. A connecting portion is connected to the trigger and to the second element and is elastically deformable in order to enable a reciprocal change of orientation between the trigger and the second element.

8 Claims, 3 Drawing Sheets

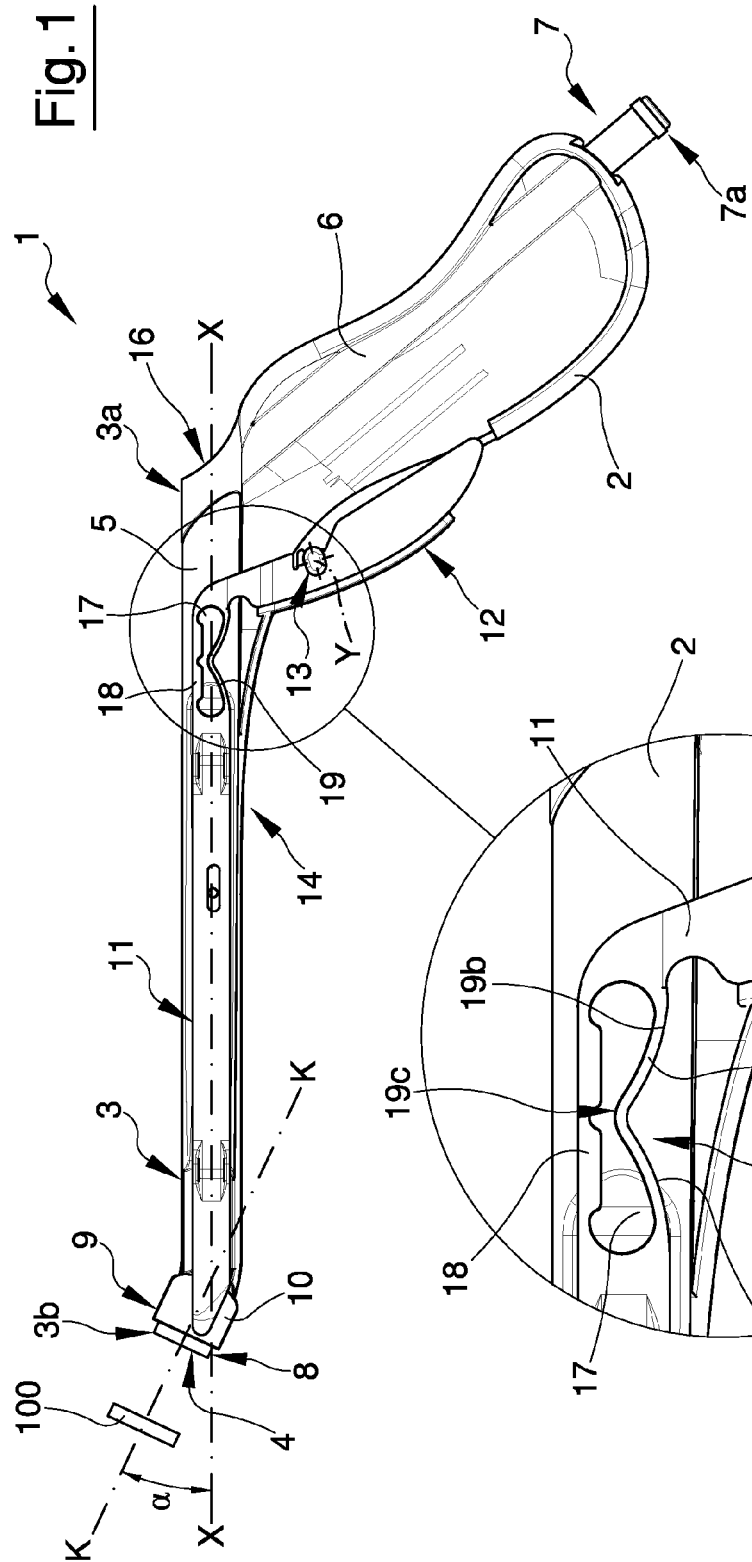

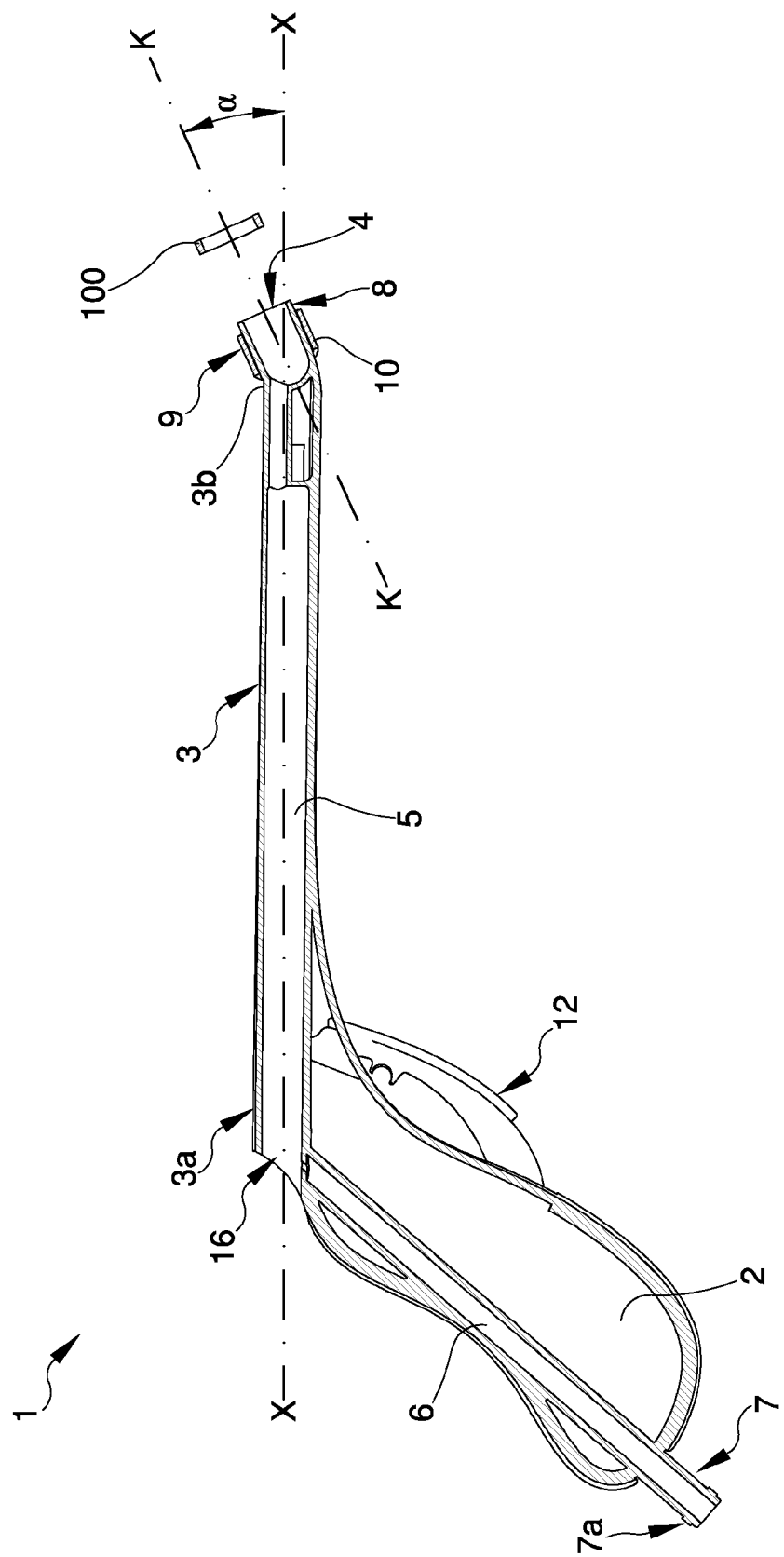

DEVICE FOR ELASTIC LIGATURE OF TISSUES

BACKGROUND OF THE INVENTION

The invention relates to a device for elastic ligature of tissues, and is particularly applicable in treatment of hemorrhoids.

Devices are known which release rubber rings, and comprise a command tube connected to a maneuvering handle and support one or more rubber rings to be released.

The command tube comprises an internal tube on a free end of which the rubber ring is predisposed, and an external tube moved in advancement with respect to the internal tube in order to determine release of the rubber ring. The handle is fixed to the internal tube and exhibits a trigger which can be manually activated by an operator in order to command the advancement of the external tube.

Devices of the above-described type exhibit some complicated aspects, mainly regarding the handle and in connection with the mechanical transmission between the movement of the trigger and the advancing of the external tube. The mechanical transmission is included internally of the handle and exhibits mechanisms and return elements which transform a rotational movement of the trigger into a translational movement of the external tube.

It is also commonly known that devices for treatment of the human body must usually be of the single-use type, due to the sterilization requirements of the devices themselves.

The foregoing demonstrates that known-type devices are poorly adapted to single-use modalities, as they are complex and expensive.

In this context, the technical objective underlying the present invention is to provide a device for elastic ligature of tissues which obviates the drawbacks in the prior art as cited herein above.

In particular, the present invention aims to make available a device for elastically legating tissues which exhibits great constructional simplicity.

A further aim of the present invention is to provide a device for elastic ligature of tissues which exhibits contained manufacturing costs.

The set technical objective and the set aims are substantially attained by a device for elastic ligature of tissues comprising the technical characteristics set out in one or more of the accompanying claims.

BRIEF DESCRIPTION OF THE DRAWINGS

Further characteristics and advantages of the present invention will better emerge from the following non-limiting description of a preferred but not exclusive description of a device for elastic ligature of tissues, as illustrated in the accompanying figures of the drawings, in which:

FIG. 1 is a lateral view of a device of the present invention;

FIG. 2 is an enlarged lateral and partly-sectioned view of a detail of the device of FIG. 1;

FIG. 3 is a lateral view in section of a device of FIG. 1;

DESCRIPTION of the PREFERRED EMBODIMENTS

Figure 4:
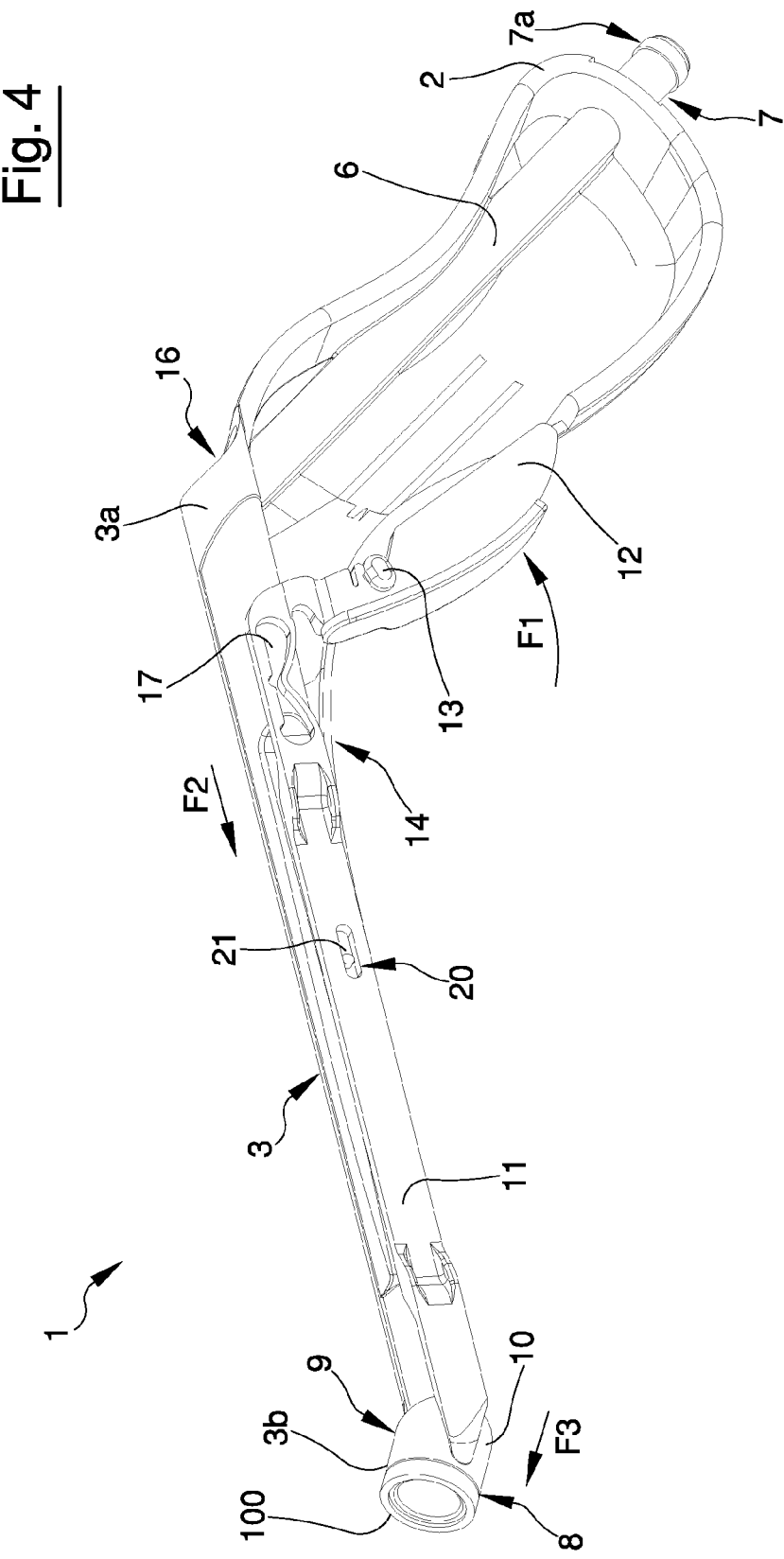
FIG. 4 is a perspective view of the device of FIG. 1.

In the figures of the drawings, 1 denotes in its entirety a device for elastic ligature of tissues such as, for example, the anal mucosa of a patient. The application is advantageously applied in treatment of hemorrhoidal complaints related to the mucosa.

The device 1 comprises a handle 2 for a user to grip, and further comprises an elongate first element 3, preferably tubular and having a circular section, destined together with the handle to give the device 1 an overall pistol confirmation.

The first element 3 exhibits a prevalent development direction X-X.

The first element 3 exhibits a proximal end 3a, arranged at the handle 2 and provided with a rear opening 16 and a distal end 3b provided with a frontal opening 4.

The first element 3 internally exhibits a chamber 5 which extends substantially along the whole development of the first element 3 and which is in communication with the frontal opening 4 and the rear opening 16.

The chamber 5 exhibits, opposite to the frontal opening 4, a rear opening 16 located at the distal end 3b.

The chamber 5 is further connectable to a pneumatic aspiration source, not illustrated, by means of as aspirating conduit 6 realised internally of the handle 2 and equipped with a connecting terminal 7. The connection terminal 7 exhibits surface reliefs 7a for improving a coupling with a connecting tube with a pneumatic aspiration source. By means of the action of the pneumatic aspiration transmitted by the aspiration conduit, and in combination with the closing of the rear opening 16 by the operator, a desired quantity of mucosa can be drawn through the frontal opening 4 internally of the chamber 5.

The distal end 3b of the first element 3 exhibits a development along an inclined direction K-K.

The inclined direction K-K defines, with respect to the prevalent development direction X-X, an angle α comprised between 0 and 30 degrees, preferably 25 degrees.

At the distal end 3b the first element 3 exhibits a support portion 8 for one or more rubber rings 100. The support portion 8 is preferably defined by a portion of the external surface of the first element 3.

The device 1 further comprises a second element 9 predisposed on the first element 3 such that the two elements 3, 9 are slidably coupled along the inclined direction K-K.

The second element 9 comprises an active portion 10, which is substantially tubular and keyed on the first element 3 in order to slide along the inclined direction K-K.

The second element further comprises an elongate connecting rod 11 developing substantially along the prevalent development direction X-X of the first element 3. The connecting rod 11 is fixed at an end thereof to the active portion 10.

The device 1 comprises a trigger 12 hinged to a frontal portion of the handle 2 such as to rotate about a hinge axis Y. In particular, as illustrated in FIG. 2, the handle 3 exhibits a cylindrical portion 13 snap-fittable to a corresponding cylindrical seating of the trigger 12. The snap-fit coupling is done by reciprocal nearing between the trigger 12 and the handle 3 along a substantially parallel direction to the prevalent development direction X-X of the element 3.

The trigger 12 acts on the second element 9 to realize a translation of the second element 9 following a rotation of the trigger 12 about the hinge axis Y.

In particular, the trigger 12 causes an axial sliding of the connecting rod 11 with respect to the first element 3 when the trigger 12 is pressed by the user.

The sliding is done parallel to the prevalent direction X-X of the first element.

The sliding of the connecting rod 11 contemporaneously causes an advancement of the second element 9 towards the distal end 3b of the first element 3.

The advancement is done along the inclined direction K-K.

The advancement of the second element 9 towards the distal end 3b of the first element 3 takes place when the trigger 12 is pressed by the user.

The advancement of the second element 9 causes release of an elastic ring 100 from the support portion 8.

In order to guarantee a correct axial sliding of the connecting rod 11, a slot 20 is afforded on the connecting rod 11, which slot 20 is mobile on a pin 21 solidly constrained to the first element 3 and crossing the slot 20.

The pin 21, during the sliding of the connecting rod 11, maintains the connecting rod 11 constantly parallel to the prevalent development direction X-X of the first element. The device 1 advantageously comprises a flexible connecting portion 14, which in particular is elastically deformable and is active between the trigger 12 and the second element 9 in order to enable a variation in the reciprocal orientation between the trigger 12 and the second element 9.

As can be seen in FIG. 2, the device 1 comprises a first connecting portion 14, solidly constrained to the connecting rod 11 and connecting the connecting rod 11 to the trigger 12.

The connecting portion 14 comprises a window 17 which is superiorly closed by an upper strip 18 and inferiorly closed by a lower strip 19.

The window 17 defines a pre-weakened zone, i.e. a zone having a lower flexional rigidity and destined to give greater elastic deformability to the strips.

In FIG. 2, each upper strip 18 exhibits a linear development, while the lower strip 19 exhibits an arched development.

In more detail, the lower strip 19 is defined by two arched tracts 19a, 19b, which are reciprocally joined to define a peak 19c located in proximity of the upper strip 18.

The conformation of the window 17 is particularly suitable for containing the compression and flexion stresses induced by the trigger 12 on the connecting rod 11, and for increasing the working life of the device.

The rotation of the trigger 12 about the hinge axis Y generates an axial component and a radial component on the connecting rod 11.

The axial component is absorbed by the lower strip 19, which the radial component is absorbed by the upper strip 18.

As the connecting portion 14 is fixed to the trigger 12 in an upper portion of the trigger 12, the connecting rod 11 can remain adjacent to the first element 3, giving a compact structure to the device 1.

The connecting portion preferably exhibits a compressive rigidity that is sufficient to determine a sliding movement of the second element 9 with respect to the first element 3, while it exhibits a flexional rigidity which is sufficiently small to enable the connecting portion 14 to absorb de-alignment between the trigger 12 and the second element 9.

The de-alignments are further controlled by the slot 20-pin 21 system, respectively present on the connecting portion 11 and the first element 3.

The dealignments between the trigger 12 and the second element 9 are due to the fact that the trigger 12, as it rotates, lowers the point of application of the thrust on the connecting portion with respect to the second element 9.

The trigger 12 and the connecting portion 14 define command means of the reciprocal movement of the first element 3 and the second element 9.

The connecting portion 14 is advantageously realised in a single piece with the second element 9 and the trigger 12. In other words, the three elements are realised in a single element, made for example of a plastic material via an industrial injection-molding process.

In a further embodiment, not illustrated, the trigger 12 and the connecting portion 14 can be solidly constrained to the first element 3 (internal) while the second element 9 (external) is fixed to the handle 2.

The device is entirely made of a plastic material, preferably polycarbonate. Further, the device 1 is preferably entirely made using an industrial injection molding process.

The device 1 functions as follows.

The device is arranged in such a position as to place the distal end 3b of the first element 3 is a position facing a portion of the mucous membrane, for example the anal mucosa.

The pneumatic aspiration is then activated and, by closing the rear opening 16, a depression is transmitted into the chamber to draw a portion of the mucosa internally of the chamber 5 through the frontal opening 4. The aspiration can be reduced or halted when a sufficient quantity of mucous membrane has been drawn into the chamber 5 through the opening and the rear opening 16 can be closed, which the operator performs by applying a finger thereto.

The device 1 is equipped with at least a rubber ring 100 which is stretched about the support portion 8. The positioning of the rubber ring 100 on the support portion 8 can be realised by a mounting cone of a substantially known type and therefore not illustrated.

Then, starting from the configuration of FIG. 1, in which a rubber ring 100 is arranged on the support surface 8, the trigger 12 is activated by pressure exerted by a user's finger and consequently the trigger 12 rotates about the hinge axis Y (the arrow F1 in FIG. 3). The pressure is in particular exerted in the rear part of the trigger 12, i.e. on the opposite side of the connecting portion 14 with respect to the hinge axis Y.

The rotation of the trigger 12 generates a thrust on the connecting portion 14 which causes the connecting portion 11 to slide with respect to the first element (arrow F2 of FIG. 4) and at the same time advances the active portion 10 of the second element 9 with respect to the first element 3 (arrow F3 of FIG. 4), pushing the rubber ring 100 beyond the support surface 8 and thus releasing the rubber ring 100 onto the portion of mucosa. The rubber ring 100, by its elastic recall effect, closes, gripping a part of the mucosa and interrupting the blood flow to the portion of mucosa connected thereto and still present in the chamber 5.

The elastic deformability of the connecting portion 14 enables an automatic recall of the trigger 12 and the second element 9 into the initial position of FIG. 1. The device 1 can then be retracted for a new application on the same patient (and in this case it is preferable that at least a further rubber ring has been predisposed on the support portion 8).

The device 1 is of the single-use type, i.e. it is packed in a sterile environment and can be used on a single patient, and must be discarded after use.

The invention thus attains the set aims, and obviates any drawbacks noted in the prior art.

The device exhibits notable constructional simplicity which translates into low production and assembly costs. The device can in fact be made of only two components, the handle solidly constrained to the first element and the trigger solidly constrained to the connecting portion and the second element.

Assembly is extremely simple, and merely requires nearing the two components along the prevalent reciprocal sliding direction between the first element and the second element. This enables reciprocal engaging between the first element and the second element, and at the same time enables a snap-fitting of the trigger on the handle.

What is claimed is:

1. A device for elastic ligature of tissues, comprising:
a first element and a second element, one of which exhibits a support portion for at least a rubber ring, the first and second elements being slidably coupled to one another such that a reciprocal sliding between the first and second elements determines a release of a rubber ring from the support portion;
a command component, manually maneuverable by an operator and acting on at least the second element for realising the reciprocal sliding between the first and second elements, the command component comprising a trigger which is activatable by the operator;
the trigger being hinged to a gripping handle of the device so as to be rotatable through an arc about a hinge axis,
wherein the command component further comprises a connecting portion, connected to the trigger and to the second element and being elastically deformable,
the trigger, the connecting portion and the second element being integrally formed as a single piece, wherein the connecting portion includes a window between a lower strip and an upper strip of the connecting portion, the lower strip being opposite the upper strip, so that the window provides a pre-weakened zone allowing the operator to change the trigger's orientation relative to the second element when the trigger is rotated about the hinge axis.

2. The device of claim 1, wherein the second element is arranged externally of the first element and wherein the first element is fixed to the gripping handle.

3. The device of claim 1, wherein the second element exhibits an active portion keyed on the first element and a connecting rod fixed on a side thereof to the active portion and on another side thereof to the connecting portion.

4. The device of claim 1, wherein the first element internally exhibits a chamber which is connectable to means for generating pneumatic aspiration, and further exhibits a front opening destined to aspirate a portion of mucous membrane into the chamber by action of the pneumatic aspiration.

5. The device of claim 1, wherein the trigger is rotatably applied to the gripping handle by means of a snap-fit coupling realisable by a nearing movement of the trigger to the gripping handle along a substantially parallel direction to a reciprocal sliding direction of the first element and the second element.

6. The device of claim 1, wherein the first element and the second element exhibit respective tubular portions, one of which exhibits the support portion.

7. The device of claim 1, wherein the upper strip has a linear conformation and the lower strip has an arched conformation.

8. The device of claim 1, wherein the lower strip is defined by two arched tracts which are reciprocally joined to define a peak projecting towards the upper strip.

* * * * *